US007267813B2

(12) United States Patent
Watanabe et al.

(10) Patent No.: US 7,267,813 B2
(45) Date of Patent: *Sep. 11, 2007

(54) INHALATION PARTICLES INCORPORATING A COMBINATION OF TWO OR MORE ACTIVE INGREDIENTS

(75) Inventors: Wiwik Watanabe, Sunnyvale, CA (US); Esko Kauppinen, Helsinki (FI); Petri Ahonen, Koisjärvi (FI); David Brown, Helsinki (FI); Esa Muttonen, Espoo (FI)

(73) Assignee: Orion Corporation, Espoo (FI)

( * ) Notice: Subject to any disclaimer, the term of this patent is extended or adjusted under 35 U.S.C. 154(b) by 472 days.

This patent is subject to a terminal disclaimer.

(21) Appl. No.: 10/398,373

(22) PCT Filed: Oct. 5, 2001

(86) PCT No.: PCT/FI01/00863

§ 371 (c)(1),
(2), (4) Date: Aug. 14, 2003

(87) PCT Pub. No.: WO02/28377

PCT Pub. Date: Apr. 11, 2002

(65) Prior Publication Data

US 2004/0028619 A1 Feb. 12, 2004

(30) Foreign Application Priority Data

Oct. 6, 2000 (FI) ................................. 20002215

(51) Int. Cl.
*A61K 9/14* (2006.01)
*A61K 9/12* (2006.01)
*A61K 31/56* (2006.01)

(52) U.S. Cl. .......................... 424/46; 424/45; 424/489; 514/171; 514/174; 514/826

(58) Field of Classification Search .................. 424/46, 424/45, 489; 514/171, 174, 826
See application file for complete search history.

(56) References Cited

U.S. PATENT DOCUMENTS

| | | | | |
|---|---|---|---|---|
| 4,590,206 | A | 5/1986 | Forrester et al. | |
| 4,999,182 | A | 3/1991 | Baumard et al. | |
| 5,637,620 | A | 6/1997 | Trofast et al. | |
| 5,674,860 | A | 10/1997 | Carling et al. | |
| 5,972,919 | A | 10/1999 | Carling et al. | |
| 6,030,604 | A | 2/2000 | Trofast | |
| 6,051,257 | A | 4/2000 | Kodas et al. | |
| 6,287,540 | B1 | 9/2001 | Trofast | |
| 6,482,438 | B1 * | 11/2002 | Singh et al. | 424/489 |
| 2004/0052732 | A1 | 3/2004 | Watanabe et al. | |
| 2004/0096516 | A1 | 5/2004 | Musa et al. | |

FOREIGN PATENT DOCUMENTS

| | | | |
|---|---|---|---|
| EP | 0357005 | A1 | 3/1990 |
| EP | 416950 | A1 | 3/1991 |
| EP | 416951 | A1 | 3/1991 |
| WO | WO93/11743 | | 6/1993 |
| WO | WO97/36574 | | 10/1997 |
| WO | WO98/41193 | | 9/1998 |
| WO | WO 00/48587 | | 8/2000 |
| WO | WO 01/49263 | A1 | 7/2001 |

OTHER PUBLICATIONS

D. Bouros et al., "Formoterol and beclomethasone versus higher dose beclomethasone as maintenance therapy in adult asthma," Eur Respir J, vol. 14, pp. 627-632, 1999.

* cited by examiner

*Primary Examiner*—Johann Richter
*Assistant Examiner*—Mina Haghighatian
(74) *Attorney, Agent, or Firm*—Finnegan, Henderson, Farabow, Garrett & Dunner, LLP

(57) ABSTRACT

Crystalline spherical inhalation particles incorporating a combination of two or more different active ingredients and a process for the preparation thereof. The particles have a narrow particle size distribution, rough surfaces and improved stability. The inhalation particles of the invention are particularly useful in the administration of a combination medicament, e.g. a combination of an anti-inflammatory agent and a bronchodilator, by inhalation in the treatment of asthma and other respiratory disorders.

20 Claims, 7 Drawing Sheets

INHALATION PARTICLES INCORPORATING A COMBINATION OF TWO OR MORE ACTIVE INGREDIENTS

This application is a U.S. national stage filing of PCT International Application No. PCT/FI01/00863, filed on Oct. 5, 2001. This application also claims the benefit of priority under 35 U.S.C. 119(a) to Finnish patent application no. 20002215, filed on Oct. 6, 2000.

FIELD OF THE INVENTION

The present invention relates to inhalation particles and inhalation compositions suitable for pulmonary drug delivery and to methods for the preparation thereof. In particular, the present invention relates to inhalation particles incorporating a combination of two or more different active ingredients. The inhalation particles of the invention are particularly useful in the treatment of asthma and other respiratory disorders.

BACKGROUND OF THE INVENTION

Inhalation has become the primary route of administration in the treatment of asthma. This is because, besides providing direct access to the lungs, medication delivered through the respiratory tract provides rapid and predictable onset of action and requires lower dosages compared to the oral route.

There have been recent advances in the treatment of asthma resulting from the recognition that asthma is a chronic inflammatory disease. Current asthma drugs can be classified into two classes, namely anti-inflammatory agents and bronchodilators. Anti-inflammatory drugs, such as glucocorticosteroids do not relieve asthma symptoms once they occur, rather they are used to control the inflammation. One of the drawbacks of anti-inflammatory drugs is that their onset of-action is relatively slow. Therefore, patients often do not recognise any immediate therapeutic effects and tend to stop the medication. This could cause the inflammation uncontrollable. On the other hand, bronchodilators, such as $\beta_2$-agonists and theophylline, are effective to relieve acute asthma symptoms. They have a potent bronchodilating activity and rapid onset of action. The short-acting inhaled $\beta_2$-agonists e.g. salbutamol and terbutaline, are important for an immediate symptomatic asthma relieve, while long-acting $\beta_2$-agonists, e.g. salmeterol, formoterol and procaterol, are important for the treatment of moderate and severe asthma. However, there are currently debates on the safety of a regular use of $\beta_2$-agonists as well as efficiency of long-acting $\beta_2$-agonists. Also, the short-acting nature of the drug requires more frequent drug administrations, which tend to cause patient compliance problem.

To overcome these problems, inhalation compositions comprising a combination of anti-inflammatory and bronchodilator agents have been proposed as described e.g. in patent publications EP 0416950, EP 0416951, WO 93/11773 and WO 98/15280. Such combinations include salmeterol with beclomethasone dipropio-nate, salmeterol with fluticasone propionate, and formoterol with budesonide. These patent publications disclose a method of mixing mechanically the two drug powders and optionally the carrier material in a certain proportion and placing the resulting inhalation powder into an inhaler device. When these combinations are used in dry powder inhalers, the consistency of drug proportion in each dose cannot be easily controlled. The ratio of drugs in each dose significantly depends on the forces existing in each drug, between the drugs, between the drug and carrier material, and between the drug and the dry powder container of the inhaler device. It is well acknowledged that the current powder manufacturing methods, especially the conventional methods, produce dry powder that is highly charged and therefore very cohesive. Hence, it is not easy to keep the ratio of the drugs in each dose constant. The inconsistency of the dose could cause serious problems especially when a very potent drug is delivered in a much higher amount than expected.

A method for the preparation of inhalation particles by spraydying a solution of one or several drugs has been disclosed in U.S. Pat. No. 4,590,206. However, the method produces amorphous particles, which have stability problems and a high, tendency toward moisture re-absorption, which is undesirable for pharmaceutical particles intended for administration by inhalation. Furthermore the size and the morphology of the particles obtained are not optimal for pulmonary delivery.

The object of the invention is to provide a composition that is better adapted than products of the prior art, for delivery of a drug combination into the lungs.

SUMMARY OF THE INVENTION

It has now been found that, by using an aerosol flow reactor method, it is possible to prepare uncharged, spherical and crystalline inhalation particles incorporating, in an individual particle, a combination of two or more drugs in a predetermined and constant ratio. The particles provide more controlled delivery of combination medicaments by inhalation, since it is now possible to keep the ratio of the drugs in each dose constant The particles exhibit improved dispersibility and good stability as a result of their crystalline nature. The particles have a narrow aerodynamic particle size distribution, typically between about 1-5 µm, which is especially suitable for the preparation of compositions for dry powder inhalers. Moreover, particle surfaces are spherical and generally rough, which reduces the force required to break-up the aggregates of the particles or detach the particle from a coarse carrier. Furthermore, the method of the invention provides a high purity product since the product purity only depends on the purity of solution precursors. Moreover, the method is simple and can be easily scaled-up to higher production rates.

In one aspect the present invention provides inhalation particles incorporating a combination of two or more different active ingredients, wherein said particles are spherical and at least one of the active ingredients is in crystalline form The mean mass aerodynamic diameter of the particles is typically between about 0.5-10 µm, more typically between about 1-5 µm The aerodynamic particle size distribution of said particles is typically between about 0.5-10 µm, more typically between 1-5 µm.

In another aspect the present invention provides an inhalation composition comprising particles incorporating a combination of two or more different active ingredients, wherein said particles are spherical and at least one of the active ingredients is in crystalline form. The particles may be formulated into an inhalation composition together with one or more pharmaceutically acceptable additives, diluents or carriers. Preferably, the composition is provided in the form of dry inhalation powder.

In still another aspect, the present invention provides a method for preparing particles incorporating a combination of two or more different active ingredients, comprising the steps of:

providing liquid feed stock comprising two or more different active ingredients in a predetermined ratio;
atomising said liquid feed stock to create droplets;
suspending said droplets in a carrier gas;
passing said carrier gas and droplets suspended therein through a heated tube flow reactor under predetermined residence time and temperature history; and collecting the particles produced.

The present invention is particularly useful in the preparation of combination medicaments, e.g. for the treatment of asthma and other respiratory disorders. Especially preferred drug combination is a combination of an anti-inflammatory agent and a bronchodilator, for example a combination of a glucocorticosteroid and a $\beta_2$-agonist.

DETAILED DESCRIPTION OF THE INVENTION

Figure 1A:
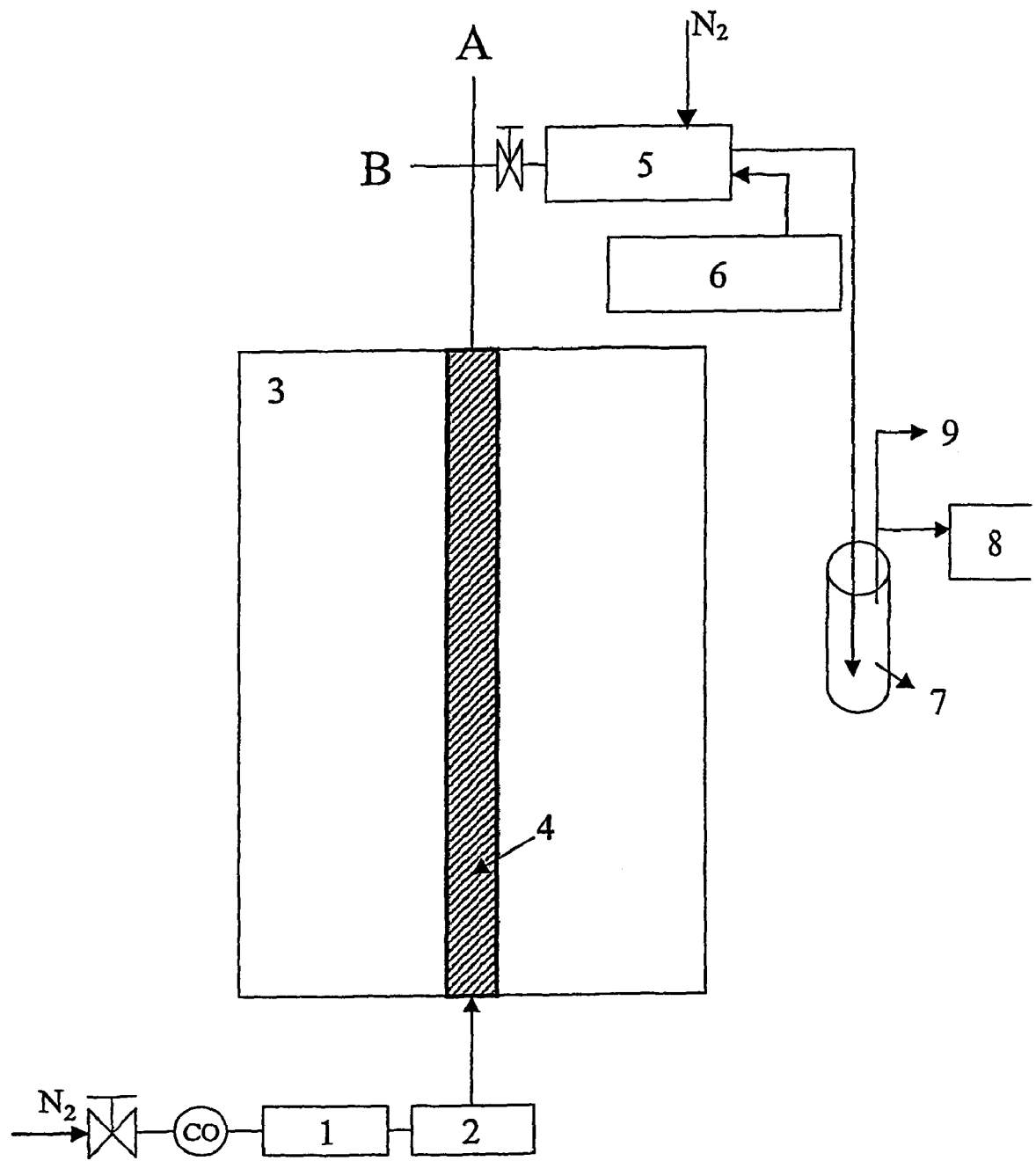
FIGS. 1a, 1b and 1c are schematic diagrams showing parts of the apparatus used in the method of the invention.

The particles of the invention can be used to deliver locally or systemically to a patient a variety of drug combinations. Particularly suitable are drug combinations which are typically used in the pulmonary delivery by inhalation, such as combinations used in the treatment of asthma and other respiratory diseases. These include, but are not limited to, a combination of an anti-inflammatory agent and a bronchodi-lator, e.g. a combination of a glucocorticosteroid and a $\beta_2$-agonist. Examples of anti-inflammatory glucocorticosteroids include beclomethasone, budesonide, fluticasone, mometasone, betamethasone, triamcinolone, flunisonide and the like and their salts and hydrates. Examples of $\beta_2$-agonists include salbutamol, formoterol, fenoterol, procaterol, salmeterol, clenbuterol and the like and their salts and hydrates. Typical combinations include beclomethasone dipropionate and formoterol fumarate, beclomethasone dipropionate and salbutamol, budesonide and formoterol fumarate, fluticasone propionate and salmeterol, beclomethasone dipropionate and salmeterol. Finding suitable ratio of the active ingredients in a given combination is considered to be a routine for one skilled in the art Any inhalable pharmaceutically active compound which can be formulated into a powder is suitable for use in the present invention. Examples of other inhalable drugs include drugs for the treatment of respiratory disorders such as anticholinergic bronchodilators such as ipratropium bromide and the like, anti-allergic drugs such as nedocromil sodium, expectorants, mucolytics, antihistarnines, cyclooxygenase inhibitors, leukotriene synthesis inhibitors, leukotriene antagonists, PLA2 inhibitors, PAF antagonists and prophylactics of asthma and combinations thereof. Alternatively, the pharmaceutically active agent can be any of several types of inhalable, systemically active drugs including anti-arrhythmnic drugs, tranquilizers, cardiac glycosides, hormones, antihypertensive drugs, antidiabetic drugs, anticancer drugs, sedatives, analgesic drugs, antibiotics, antirheumatic drugs, imrnunothera-peutics, antifungal drugs, vaccines, antiviral drugs, proteins, peptides, vitamins and combinations thereof. A combination of an anti-inflammatory agent and a broncho-dilator is particularly preferred.

The particles of the present invention are preferably prepared using an aerosol flow reactor method (aerosol synthesis method). It is a one-step continuous process, which can directly produce desirable particle size range. The method has been used to produce various materials, e.g. ceramic powder (U.S. Pat. No. 5,061,682) or zirconia powder (U.S. Pat. No. 4,999,182), at high operation temperatures. However, the method has not been used to produce pharmaceutical materials, which requires a significantly lower-temperature operation (less than 300° C.).

The aerosol flow reactor method comprises generally the following steps; (a) providing liquid feed stock comprising two or more different active ingredients in a predetermined ratio, (b) atomising said liquid feed stock to create droplets, (c) suspending said droplets in a carrier gas, (d) passing said carrier gas and droplets suspended therein through a heated tube flow reactor under predetermined residence time and temperature history, and (e) collecting the particles produced.

The above method differs significantly from the conventional spray-drying process. In spray-drying, hot gas is used as a source of heat to evaporate the solvent. The spray-drying chamber is only used as a place for the heat transfer to occur, the chamber itself is not heated. The temperature of the gas is changing across the chamber as heat transfer occurs between the cold feed and the hot gas. Furthermore, the evaporation is so rapid that it is not easy to properly control the temperature history and the residence time of each droplet and product particle. The crystallization can not be easily controlled either, and therefore the particles formed are commonly amorphous.

In the present method, the droplets are already suspended in the carrier gas before they are fed into the tubular flow reactor, which is placed in an oven set at a constant temperature. The carrier gas flows evenly in the tubular reactor with a constant rate, uniform temperature field and non-circulating flow. Therefore, the temperature history and the residence time of each droplet and product particle can be properly controlled and excellent uniformity of the particles can be ensured. Accordingly, the method provides better control of the droplet size distribution, and thus the particle size distribution such that particles with optimal aerodynamic particle size distribution typically between about 1-5 μm can be obtained. Furthermore, in contrast to spray drying, the method allows essentially complete crystallization of the particles. Thus, the method is able to produce consistent and controlled particle properties, including particle size and size distribution, shape, crystallinity, polymorphic phase, surface roughness and chemical purity.

The liquid feed stock of step (a) may be prepared by mixing each active ingredient with a suitable liquid solution, e.g. solvent. The two or more liquid feed stocks are then mixed to form a solution, suspension, dispersion, gel, emulsion, slurry or the like, and is preferably homogenous to ensure uniform distribution of the components in the mixture. It is also possible to mix all active ingredients directly in one liquid feed stock. The liquid feed stock in the form of a solution is preferred.

Various solvents may be employed in the preparation of the liquid feed stock, including but not limited to, water, hydrocarbons, halogenated hydrocarbons, alcohools, ketones and the like. Examples of suitable solvents include water, hexane, perfluorohexane, ethanol, methanol, acetone, chloroform, methylene chloride and combinations thereof.

In case the liquid feed stock is a solution, the active ingredients should be sufficiently soluble in the solvent of the solution so as to obtain, from the atomized droplets of the liquid feed stock, uniform particles with the desired particle size, size distribution and drug ratio. The total solids dissolved may be present in wide range of concentrations, typically from about 0.1% to about 10% by weight, for example from about 1% to about 5% by weight A liquid feed stock containing relatively low concentration of solids results in particles having relatively small diameter. The finding of suitable liquid feed stock concentrations for each active agents/solvent combinations is considered to be a routine to one skilled in the art. Usually, the liquid feed stock concentration is firstly chosen at its maximum solubility so as to obtain the largest particle size with the atomizer and atomizer conditions used. From the results, the liquid feed stock concentration required to obtain the desired particle size range with the atomizer and the atomizer conditions used can be approximated.

The liquid feed stock is atomized to create droplets in a suitable atomizer, which are well known in the art, such as a spray nozzle (e.g. a two fluid nozzle), an ultrasonic or air assisted nebuliser or a spinning disc, an ultrasonic nebulizer being preferred Examples of the devices used in this process include ultrasonic generators sold under trademarks Omron NE-U12 and RBI Pyrosol 7901. While there are no special restrictions placed on the atomisers used in the process, it is recommended to use an atomiser, which can produce uniform droplets of constant composition and in a specific size range. Such devices are suitable to produce dry powders of controlled composition and with particle size range suitable for dry powder inhalation.

The droplets of the liquid feed stock are suspended in a carrier gas before passing through a heated tube flow reactor. The carrier gas must be inert with respect to the drug molecules and the solvent. It is recommended to use nitrogen gas or other inert gases. The temperature of the carrier gas is typically ambient. To maintain a uniform solution concentration in the droplets in the suspending phase, it is preferred to bubble the carrier gas through a bottle containing the same solvent as the liquid feed stock before entering the atomizer.

Because the droplets are already suspended in the carrier gas when fed into the reactor (i.e. the droplet generation and flow reactor are separated), the temperature history and residence time of each droplet and product particle can be better controlled than in the conventional spraying method. Therefore, excellent uniformity of the resulted particles and narrow particle size distribution can be ensured.

The droplets suspended in the carrier gas are passed through a tubular flow reactor, which is maintained at a constant temperature. The temperature and the flow rate of the carrier gas are adjusted to evaporate the solvent and to allow the crystallization process to complete. The particles formed are then collected using an electrostatic precipitator, a cyclone, a planar filter (e.g. nylon) or other particle collecting devices.

The particle size may be controlled to any expected particle size ranges by selection of the atomizer and concentration of the liquid feed stock. It is also possible to employ a droplet size modification apparatus (e.g. impactor or virtual impactor, or using size selective collection of particles, e.g. a cyclone) upstream and/or downstream of the flow reactor.

For the tubular flow reactor, while there are no particular restrictions, it is recommended to use a vertical, rather than horizontal configuration in order to minimise buoyancy effects and related losses due to recirculating flow. A laminar flow is preferred. To ensure uniform temperature and flow fields in the hot zone of the reactor, CFD (Computational Fluid Dynamics) calculations have shown that it is preferable that the aerosol flows against gravity. Flow in any other direction tends to produce undesirable reactor conditions. The reactor tube is preferably placed inside an oven to maintain a uniform reactor wall temperature during the process. The oven can be of any kind, which has sufficient temperature control (i.e. $\pm 1°$ C. or less) at low temperatures (less than 300° C.). The temperature of the oven is set such that the materials being processed do not decompose. Typically the selected oven temperature is within the range of about 30 to 300° C., more typically between about 70 to 200° C. For the combination of beclomethasone dipropionate and formoterol fumarate, for example, since the melting point of beclomethasone dipropionate is about 210° C. and the melting point of formoterol fumarate is about 138° C., the range of oven temperature used for the combination particle production may vary between 30 to 110° C., preferably between 70 to 100° C.

While there are no particular restrictions placed on the particle collection, it is recommended to use a system, which can be heated to prevent the re-condensation process. Electrostatic precipitators, cyclones and/or filters can be used for this purpose. Accordingly, the particle collection system and the line from the flow reactor outlet to the particle collection system are preferably heated to a temperature above the boiling point of the solution to prevent the recondensation process to occur. However, the temperature should not be too high so as to cause material degradation. For example, for the combination of beclomethasone dipropionate and formoterol fumarate dissolved in ethanol, the temperature of the collection system and the line may be kept constant at a temperature between 80 to 100° C., preferably between 80 and 90° C. To further prevent the recondensation process to occur, dry carrier gas may be flown to the particle collection system. The carrier gas is preferably heated at a temperature between 80 to 90° C.

It is preferred that the aerosol flow reactor conditions are selected such that crystalline spherical particles of homogeneous constituents having a narrow particle size distribution and rough surfaces are formed. The particle size of the resulting powder is such that the mean mass aerodynamic diameter of said particles is between about 0.5-10 µm, more typically between about 1 -5 µm. Particularly it is preferred that more than 98% of the mass is in particles having a diameter of 5 µm or less, and less than about 5% of the mass being in particles having a diameter of 0.5 µm or less. It is particularly preferred that the aerodynamic particle size distribution of said particles is between about 0.5-10 µm, more preferably between about 1 -5 µm.

The particles obtained incorporate, in an individual particle, a combination of two or more drugs. An individual particle means here an unagglomerated particle which have the typical spherical form.

In the particle of the invention, at least one of the active ingredients is in a crystalline form, i.e. has a relative degree of crystallinity preferably 90% or higher, more preferably 95% or higher, most preferably 99% or higher. Preferably the aerosol flow reactor conditions are selected such that all active ingredients in the particle are in a crystalline form The relative degree of crystallinity can be determined based on the x-ray powder diffraction patterns. The value of the relative degree of crystallinity can be estimated by a known method of broadening of the diffraction maxima (FWHM-values).

The particles of the invention are essentially spherical, i.e. the spherical form is consistent and apparent when examined under a scanning electron microscope. The spherical form reduces the contact areas between particles and thereby improves aerosolization and deagglomeration of the particles upon inhalation.

Generally, the surface of the spherical particles is rough, i.e. the roughness is consistent over the entire surface of the particle, apparent when examined under the scanning electron microscope, and the ratio of the maximum and minimum diameter of the particle is between 1.001-1.5, preferably between 1.002-1.2, more preferably between 1.01-1.1. Rough surface is advantageous since it increases the effective separation distance of the particles, and thus improves aerosolization and deagglomeration properties of the particles.

If desired, various additives known in the art may be additionally incorporated in the particles together with the active ingredients. Such additives include e.g. diluents such as lactose, carriers and stabilizers and the like. In such case the additives are included in the liquid feed stock of the process together with the active ingredients. Also such additives incorporated in the particle are preferably in crystalline form. It is particularly preferred that at least about 90 w-% of the total weight of the particle is in crystalline form.

However, in order to reduce the amount of material other than the active ingredients potentially reaching the lungs, it is preferred that the active ingredients constitute at least 90 w-%, preferably at least 95 w-%, more preferably at least 99 w-%, of the total weight of particles. Most preferably the particles are free from other material than the active ingredients.

The particles of the invention may be formulated into an inhalation composition together with one or more pharmaceutically acceptable additives, diluents or carriers. Examples of suitable solid diluents or carriers comprise lactose, dextran, mannitol and glucose, lactose being preferred. Examples of aerosol carriers include non-chlorofluorocarbon-based carriers such as HFA (hydrofluoroacane). The use of aqueous carriers is also possible. Typical additives include solubilizers, stabilizers, flavouring agents, colorizing agents and preserving agents.

The particles of the invention are preferably administered in the form of a dry powder composition. The particles obtained are generally in the form of individual (unagglomerated) particles which are well suited for pulmonary drug delivery by inhalation as such, e.g. they can be filled directly into capsules, cartridges, blister packs or reservoirs of dry powder inhalers. However, if desired the particles may be adapted to form loose agglomerates of several individual particles, said agglomerates breaking into individual particles upon dispersion in the inhaled air stream. The particles may also be combined with pharmaceutically acceptable carrier materials or excipients typically used in dry inhalation powders. Such carriers may be used simply as bulking agents or to improve the dispersibility of the powder. For example, the particles may be used in admixture with carrier particles, e.g. lactose, having larger particle size than the active ingredients, typically in the range of 5 to 100 μm. If the composition contains a carrier, the total amount of the active ingredients is typically about 0.1-50% (w/w), preferably about 1-10% (w/w), based on total weight of the composition. Such compositions can be prepared by methods known in the art.

The particles of the invention can be also administered in the form of pressurized metered dose inhalation suspension, where the particles are suspended in pressurized aerosol carrier and delivered using pressurized metered dose inhaler (pMDI).

The invention is further illustrated by the following experiments, which are not meant to limit the scope of the invention.

EXPERIMENTS

All compositions produced according to the present invention fulfill the strict specification for content and purity required for pharmaceutical products.

Example 1

Preparation of Inhalation Particles Incorporating a Combination of Beclomethasone Dipropionate and Formoterol Fumarate Preparation of the Liquid Feed Stock Beclomethasone dipropionate is an anti-inflammatory glucocorticosteroid, which is practically insoluble in water, freely soluble in acetone and in chloroform, and sparingly soluble in alcohol. Thus, the solvent could be acetone, chloroform, methanol, ethanol, or other alcohols. In the current experiments, ethanol was used as a solvent, not only because ethanol is cheap and readily available but it is also recommended for use in production of pharmaceutical agents because it is non-toxic.

The beclomethasone dipropionate liquid feed stock was prepared by dissolving 1 gram of beclomethasone dipropionate powder in 40 ml of ethanol (99.5%) at room temperature.

Formoterol fumarate is a $\beta_2$agonist bronchodilator, which is freely soluble in glacial acetic acid, soluble in methanol, sparingly soluble in ethanol. Thus, the solvent could be glacial acetic acid, methanol or ethanol. In the current experiments, ethanol was used as a solvent, not only because ethanol is cheap and readily available but it is also harmless and recommended for use in production of pharmaceuticals.

The formoterol fumarate liquid feed stock was prepared by dissolving 1 gram of formoterol fumarate powder in 613 ml of ethanol (99.5%) at room temperature.

Figure 1B:
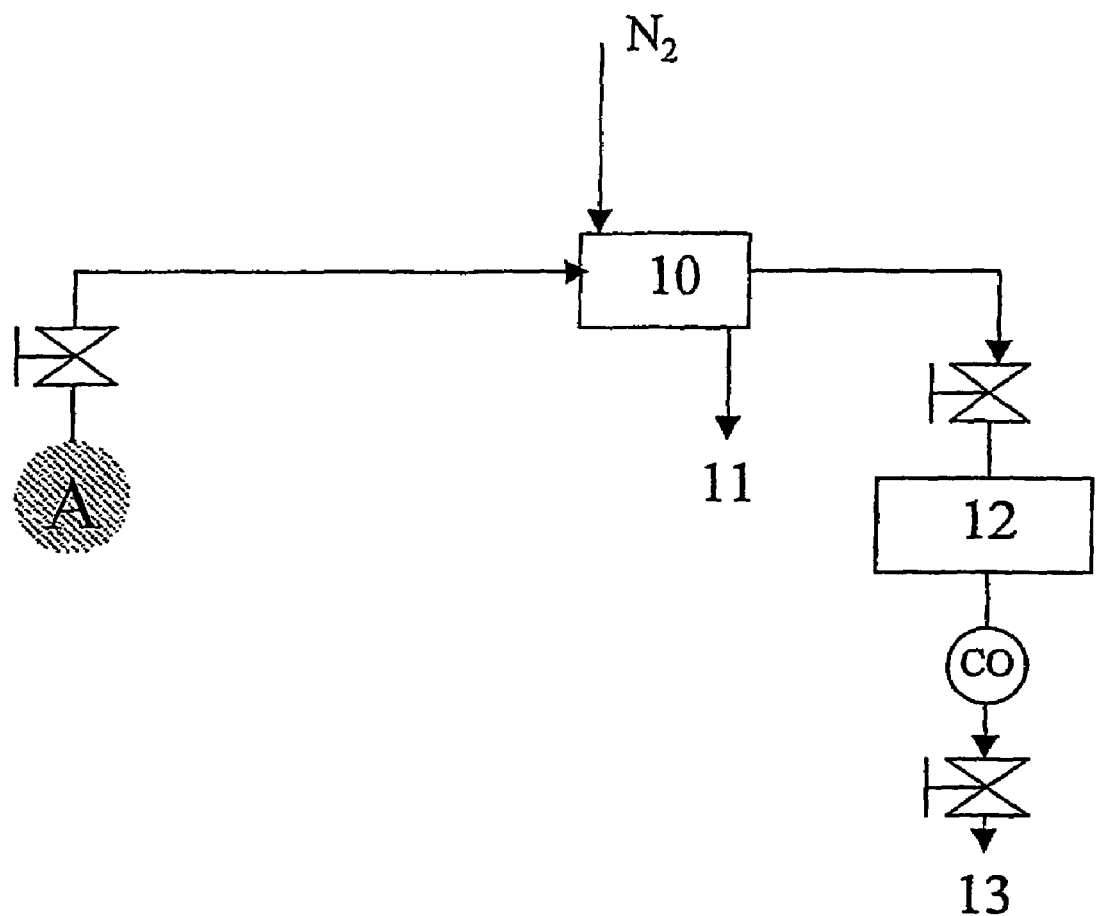
Figure 1C:
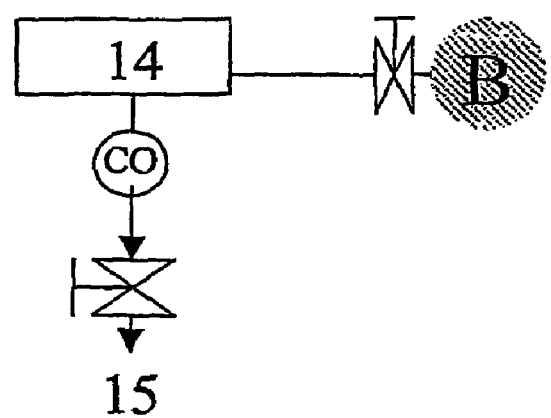

The two liquid feed stocks were then mixed in such a way that ratio between beclomethasone dipropionate and formoterol fumarate in the mixture is 200:6 (weight basis), which was considered to be a suitable drug ratio for the treatment of asthma Aerosol Synthesis FIG. 1a shows the experimental set-up of the particle synthesis, and FIG. 1b and 1c show optional configurations used for particle analysis. The liquid feed stock described above was atomised using an ultrasonic atomizer (2), sold under trademark RBI Pyrosol 7901. The resulted droplets, which were suspended into a carrer gas, were then passed through a heated tube flow reactor (4). Nitrogen gas was used as a carrier gas, with a constant flow rate of 1.5 l/min. To maintain a uniform solution concentration in the atomizer, the carrier gas was bubbled through ethanol in a saturation bottle (1) before entering the atomizer. A vertical tube, which was inserted into an oven (3), was used to dry up the droplets. The oven used was a WTB Binder FD)FED 400, which has temperature variations of ±1 and ±2° C. for temperature at 70 and 110° C., respectively. The tube was made of stainless steel, with an inner, diameter and a heated length of 30 and 800 mm, respectively. The oven temperature was set at 100° C. The minimum particle residence time in the heated zone under the selected process conditions was approximately 12 seconds. From the CFD calculation, it is shown that temperature field is uniform and the velocity is fully developed and non-circulating in the heated zone.

Figure 2:
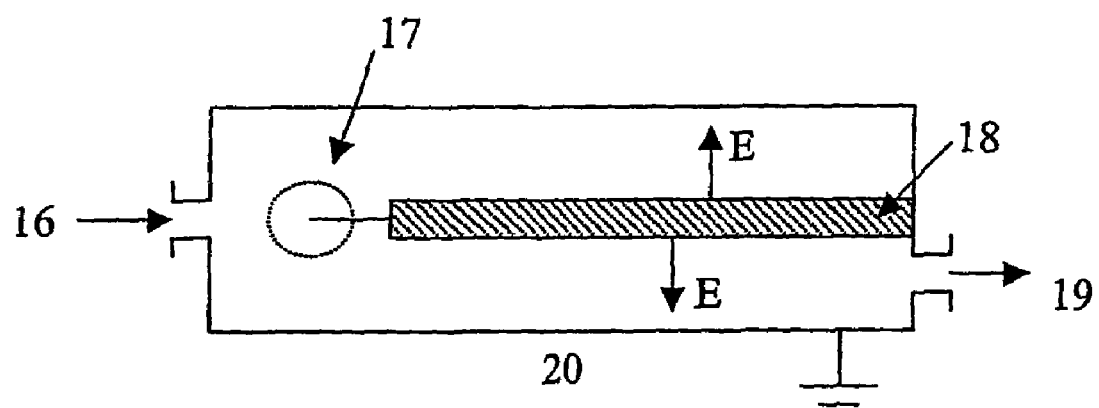
FIG. 2 is a schematic diagram of the electrostatic precipitator.

The resulted particles were then collected using an electrostatic precipitator (ESP) (5) connected to a high voltage generator (6). A carrier gas, preferably nitrogen gas, may be flown to the ESP to further prevent the recondensation process to occur. The exhaust gas was led from ESP via a dripping bottle (7) to exit (9). FIG. 2 shows the schematic diagram of ESP having inlet (16) and exit for exhaust gas (19). The ESP was made of a tubular stainless steel collection plate (20) with inside diameter and length of 10 and 50 cm, respectively. A 0.05 mm diameter tungsten wire was placed on the center axis of the collection plate and a high voltage (18) of 16 kV was applied between the wire and the plate. The high electric field formed a corona discharge (17) on the wire and charged the gas molecules. The gas ions were then formed. These ions migrated across the space between the wire and the plate under the influence of the applied electric field. During the migration, the ions collided with the aerosol particles, which thus acquired charge. The charged particles then migrated toward the grounded surface electrode. When the particles struck the grounded plate, they lost their charges and adhered to the plate surface via surface forces. Therefore, the particles collected were not charged. Dry nitrogen gas with a flow rate of 22.5 l/min was flowed into the ESP and temperature in the ESP and in the line from tubular tube outlet to the ESP were maintained at a constant temperature of 85°0 C., to avoid condensation of organic vapours and moisture to occur. Condensation particle counter (CPC) model 3022, shown as (8) in FIG. 1a, was used to determine efficiency of the ESP. Particles collected were then removed from the plate surface of ESP by scraping, and then placed in a tight glass bottle to avoid moisture penetration or other contamination.

Characterisation i. Particle Size Analysis

Figure 3A:
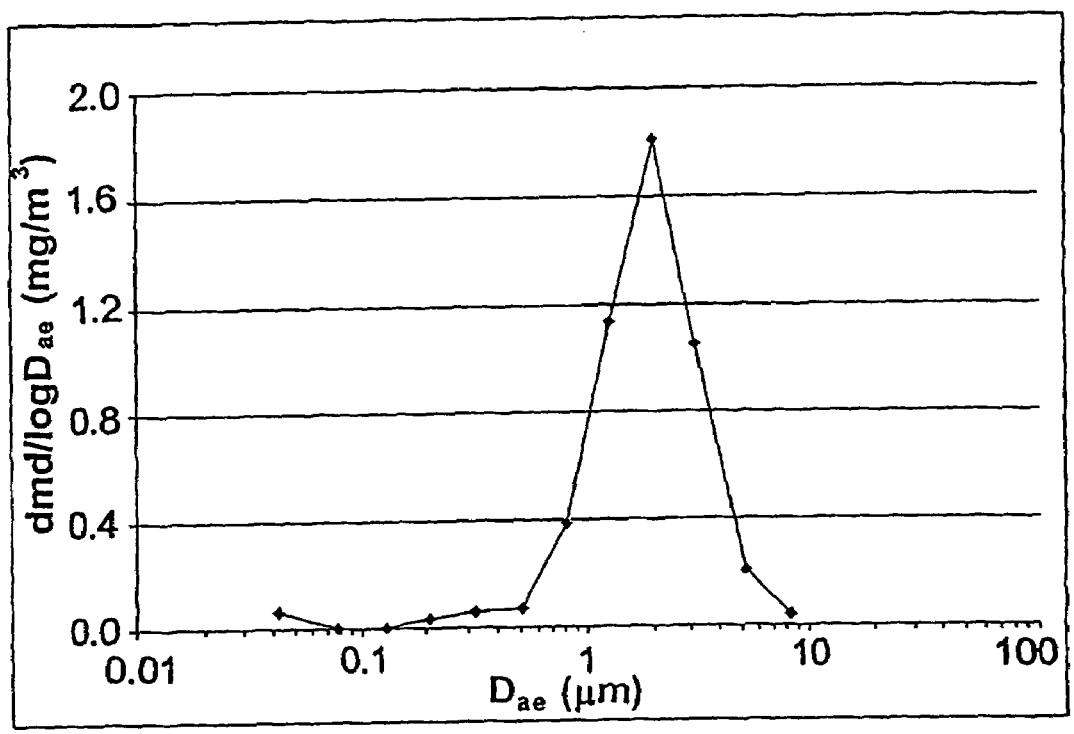
FIGS. 3a and 3b show the normalised and cumulative mass size distribution of the drug combination particles of the invention.
Figure 3B:
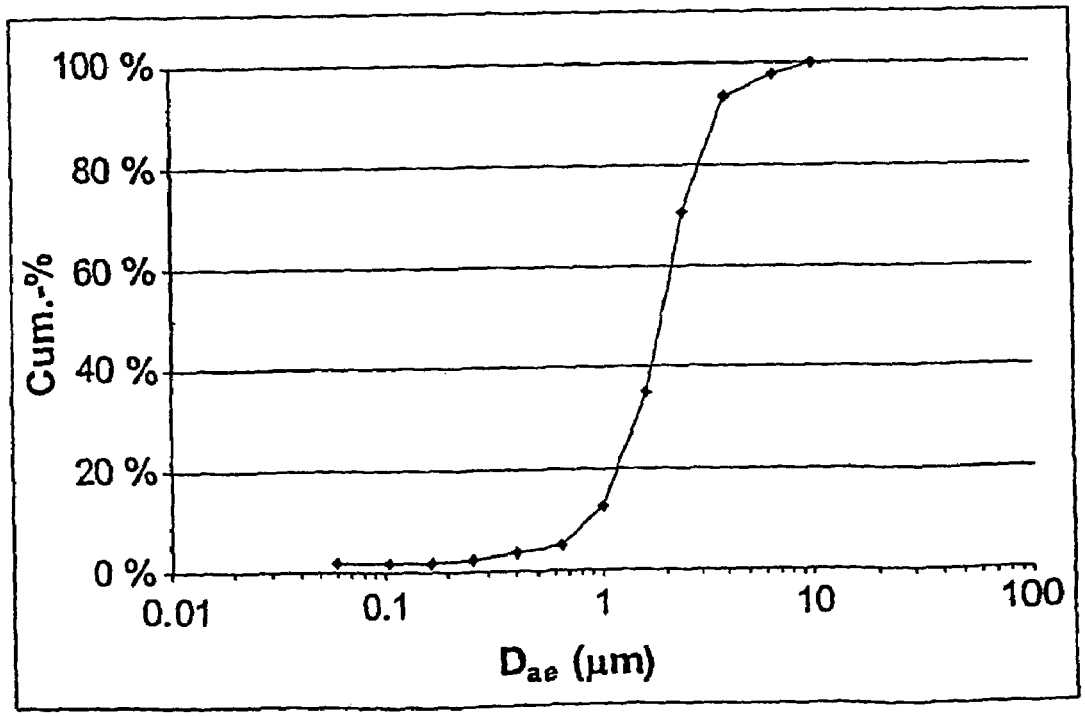
Figure 4:
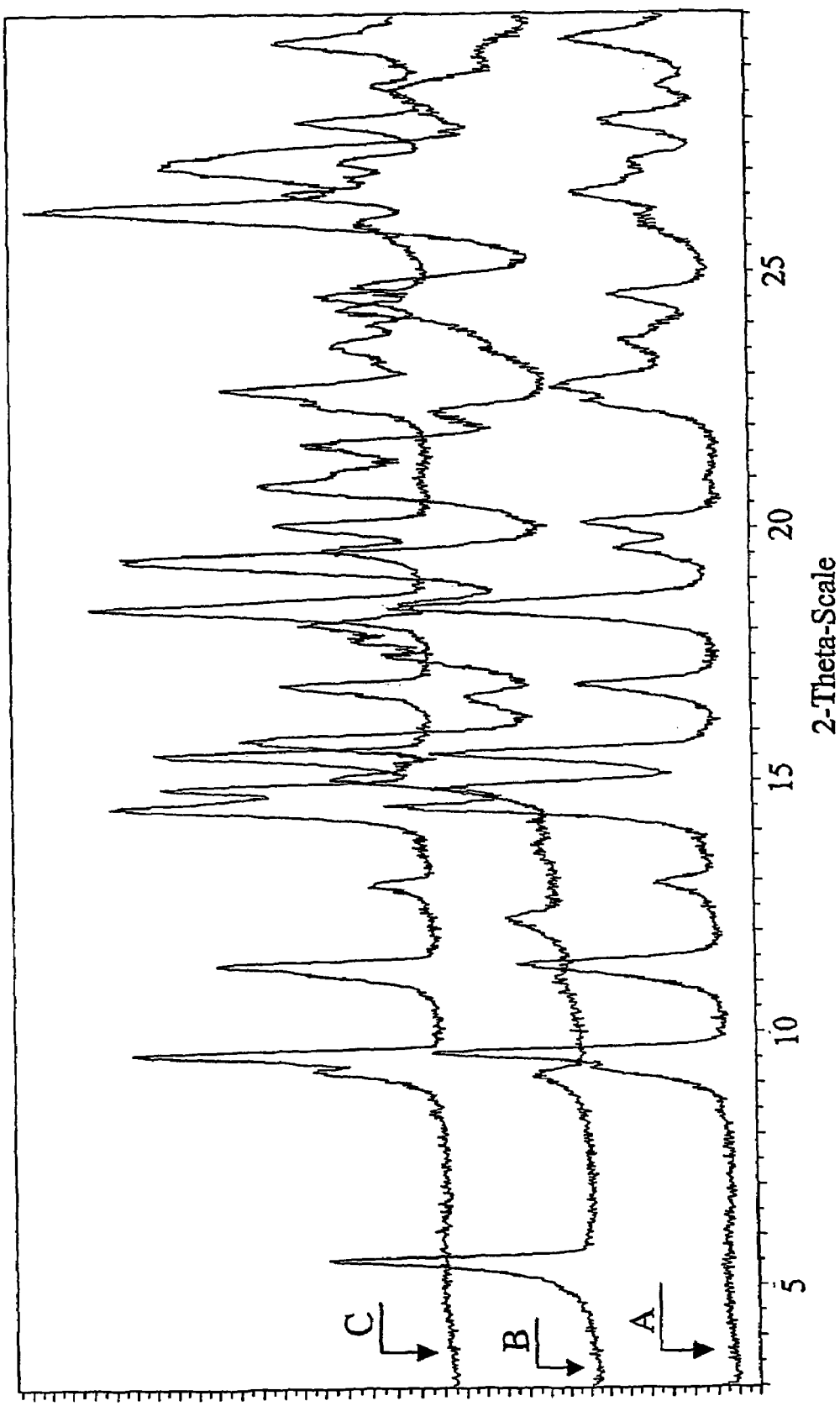
FIG. 4 shows the XRD pattern of the combination powder of the invention.
Figure 5:
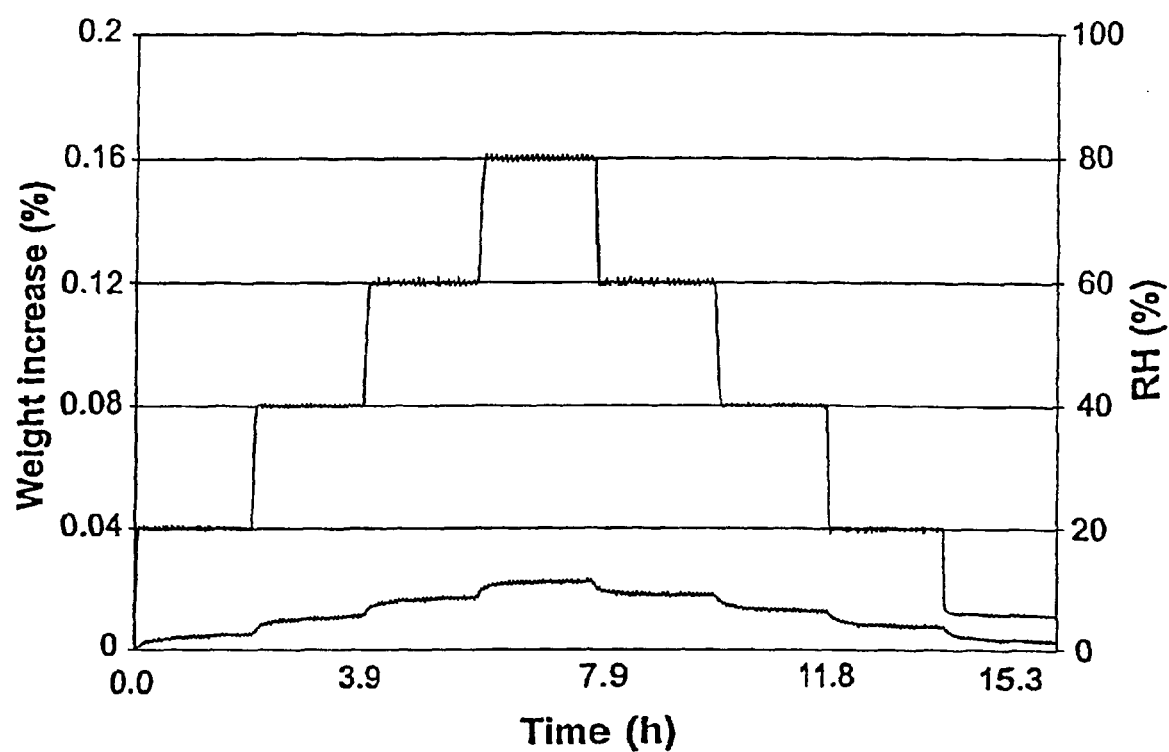
FIG. 5 shows moisture absorption profile of the combination powder of the invention when exposed in different humidity levels.
Figure 6:
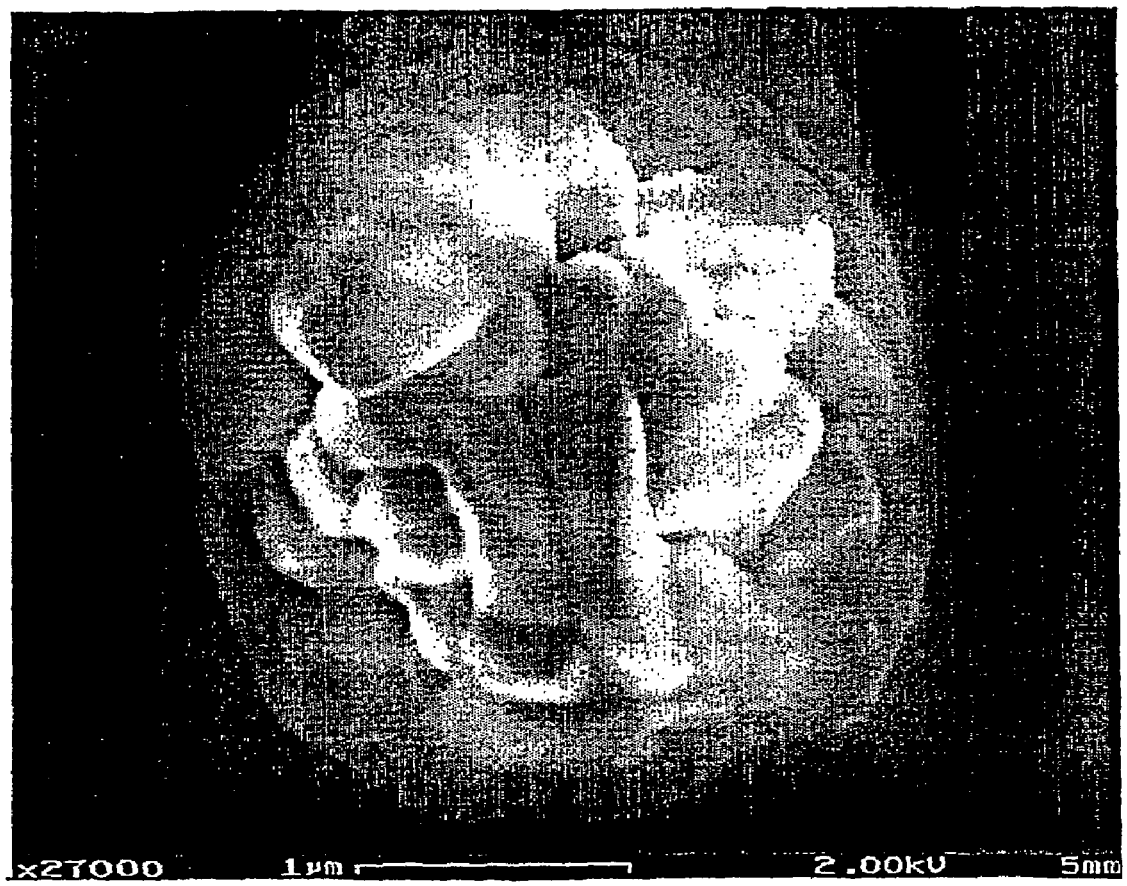
FIG. 6 depicts a scanning electron microscopy image of the combination powder of the invention.

Referring now to FIG. 1b, the particle size distribution was measured by an electrical low pressure impactor (12) (ELPI) connected to a vacuum (13). The particles exiting the tubular tube were passed into a diluter (10), with a dilution ratio of 1:10, before entering the ELPI. Exhaust gas exit (11) was arranged in the diluter. To minimize temperature gradient, and thus to reduce the moisture condensation, the diluter, the line to the diluter and the gas line into the diluter were layered with heating elements, which were kept at a temperature higher than that of the solution dew point. FIGS. 3a and 3b show normalised and cumulative mass size distributions of beclomethasone dipropionate/formoterol fumarate particles, respectively, measured gravimetrically. It is shown that a narrow size distribution within the range of aerodynamic particle size of interest, i.e. at around 1-5 μm, was obtained.

ii. Particle Crystallinity

Crystallinity of the sample was studied by X-ray powder diffraction (Diffractometer D500, Siemens GmbH, Karlsruhe, Germany). A copper target X-ray (wavelength 0.1541 nm) tube was operated with the power of 40 kV×40 mA.

For x-ray powder diffraction analysis, 500 mg of the powder was mounted to a cylindrical sample stage which has a diameter of 20 mm and height of approximately 2 mm.

The relative degree crystallinity of the powder was also determined based on the x-ray powder diffraction patterns shown in FIG. 4, wherein "A" means typical beclomethasone dipropionate, "B" means typical formoterol fumarate and "C" means the (200:6) combination of beclomethasone dipropionate (BDP) and formoterol fumarate. It is noticed that the diffraction pattern of the combination of beclomethasone dipropionate (BDP) and formoterol fumarate resembles very much to the diffraction pattern of pure BDP. Hence, formoterol fumarate may be partly or totally in amorphous state. For BDP, it can be seen that the maximum intensities were sharp and well above background intensities, which indicates that the BDP in the powder was well crystallised. The determined relative degree of crystallinity for BDP was 100%. The estimation was based on the broadening of the diffraction maxiima (FWHM-values) positioned at 11.3° and 18.4°.

iii. Powder Stability

The ratio of BDP to formoterol fumarate in the powder is 200:6 (formoterol fumarate is about 2.9% w/w). As shown from the XRD pattern, formoterol fumarate in the powder may be in amorphous state. Despite of the small formoterol concentration in the powder, it was desirable to conduct stability tests to ensure that the powder remains stable in various conditions. The stability tests were carried out by observing moisture adsorption profiles of the powder when exposed to different relative humidity levels. From FIG. 5, it can be seen that the combination powder of the invention is stable when exposed to different humidity levels, with a maximum weight increase of 0.02% when exposed to 80% relative humidity for 24 h.

iv. Particle Shape and Surface Structure

Referring now to FIG. 1*c*, individual particles were collected on the surface of a holey carbon film TEM grid (14) connected to a vacuum (15) after particle collection. The morphology of the particles were then imaged using a field emission low voltage scanning electron microscope (FE-SEM) operated at 2 kV acceleration voltage. FIG. 6 is a scanning electron microscope image of the powder (magnification ×27000). It is shown that the particles are spherical with rough surfaces and diameter of about 2-3 μm.

v. Chemical Analysis

The product purity was analysed using Hewlett_Packard HP 1090 Liquid Chromatograph equipped with diode array detector. The column used is Hewlett-Packard Hypersil ODS, 5 μm, 100×2.1 mm.

To analyse formoterol fumarate, the powder was dissolved into 25 ml of a mixture of water-methanol (25:75). The sample was then analysed using the high performance liquid chromatograph with diode array detector (wavelengths 200 nm and 214 nm), and the quantitative analyses were carried out using external standard method with four standard concentrations. Eluents used were 0.01M ammonium dihydrogen phosphate ($NH_3$ is added to obtain pH 8) (solvent A) and acetonitrile (solvent B) with gradient elution of 40% B for 2 minutes followed by 100% B in 5 minutes. The flow rate and injection volume used were 0.4 ml/min and 5 μl, respectively, and the oven temperature was set to 40° C.

To analyse beclomethasone dipropionate, the powder was dissolved into 25 ml of a mixture of water-methanol (25:75) and then diluted (1:50) using water-methanol (25:75). Samples were then analysed with the high performance liquid, chromatograph using diode array detector (wavelength 241 nm) and quantitative analyses were carried using external standard method (four different standard concentrations). Eluents used were water (solvent A) and acetonitrile (solvent B) with gradient elution of 65% B for 2 minutes followed by 100% B in 5 minutes. The flow rate and injection volume used were 0.4 ml/min and 8 μl, respectively, and the oven temperature was set to 40° C.

The analysis results show beclomethasone dipropionate 97.1% and formoterol fumarate 2.9%, the same as concentration of solution precursor.

Example 2

Dry Inhalation Powder

|  | Per dose |
|---|---|
| Formoterol fumarate | 6 μg |
| Beclomethasone dipropionate | 200 μg |
| Lactose monohydrate Ph. Eur. | 8 mg |

Particles of Example 1 and part of lactose is added into a blender. The powder mixture is mixed until it is homogenous. The mixture is sieved to reduce the number of particle clusters present. Thereafter the rest of lactose is added and the powder is again mixed until it is homogenous. Powder is poured into a supply chamber of the multi-dose powder inhaler Easyhaler (Orion Corporation trademark) for a supply of 200 doses.

The invention claimed is:

1. Inhalation particles incorporating, in an unagglomerated individual particle, a combination of two or more different active ingredients, wherein the active ingredients are an anti-inflammatory drug and a bronchodilator wherein said particles are spherical and at least one of the active ingredients is in crystalline form.

2. Inhalation particles according to claim 1, wherein the mean mass aerodynamic diameter of said particles is about 1-5 μm.

3. Inhalation particles according to claim 1, wherein the aerodynamic particle size distribution of said particles is about 0.5-10 μm.

4. Inhalation particles according to claim 1, wherein the ratio of the active ingredients is constant.

5. Inhalation particles according to claim 1, wherein the particles have a rough surface.

6. Inhalation particles according to claim 1, wherein the particles are uncharged.

7. Inhalation particles according to claim 1, incorporating a combination of beclomethasone dipropionate and formoterol fumarate.

8. An inhalation composition comprising particles incorporating, in an unagglomerated individual particle, a combination of two or more different active ingredients, wherein the active ingredients are an anti-inflammatory drug and a bronchodilator wherein said particles are spherical and at least one of the active ingredients is in crystalline form.

9. An inhalation composition according to claim 8 additionally comprising one or more pharmaceutically acceptable additives, diluents or carriers.

10. An inhalation composition according to claim 8 in the form of dry inhalation powder.

11. An inhalation composition according to claim 8 in the form of pressurized metered dose inhalation suspension.

12. An inhaler device comprising an inhalation composition according to claim 8.

13. A method for preparing particles incorporating, in an unagglomerated individual particle, a combination of two or more different active ingredients wherein the active ingredients are an anti-inflammatory drug and a bronchodilator comprising the steps of:

providing liquid feed stock comprising two or more different active ingredients in a predetermined ratio:

atomising said liquid feed stock to create droplets:

suspending said droplets in a carrier gas;

passing said carrier gas and droplets suspended therein through a heated tube flow reactor under predetermined residence time and temperature history; and collecting the particles produced.

14. A method of claim 13 wherein the liquid feed stock, comprising two or more different active ingredients in a predetermined ratio, is in the form of a solution.

15. A method according to claim 13, wherein the carrier gas is selected from nitrogen gas or other inert gas.

16. A method according to claim 13, wherein the particles are collected using a particle collection system selected from an electrostatic precipitator, a cyclone or a filter.

17. A method according to claim 16, wherein the particle collection system is heated to a temperature above the boiling point temperature of the solution to prevent condensation.

18. A method according to claim 13, wherein the liquid feedstock comprises beclomethasone dipropionate and formoterol fumarate as active ingredients.

19. A method according to claim 18, wherein the liquid feed stock comprises ethanol as a solvent.

20. Inhalation particles according to claim 1, wherein the aerodynamic particle size distribution of said particles is about 1-5 μm.

* * * * *